United States Patent
Schweinsberg et al.

(10) Patent No.: US 9,167,811 B2
(45) Date of Patent: Oct. 27, 2015

(54) BAIT FORMULATIONS FOR CONTROLLING SLUGS AND SNAILS

(75) Inventors: Otto Schweinsberg, Rheinböllen (DE); Arthur Ziegler, Kirschroth (DE)

(73) Assignee: Compo GmbH, Munster (DE)

( * ) Notice: Subject to any disclaimer, the term of this patent is extended or adjusted under 35 U.S.C. 154(b) by 10 days.

(21) Appl. No.: 13/697,863

(22) PCT Filed: May 13, 2011

(86) PCT No.: PCT/EP2011/057751
§ 371 (c)(1),
(2), (4) Date: Feb. 5, 2013

(87) PCT Pub. No.: WO2011/141566
PCT Pub. Date: Nov. 17, 2011

(65) Prior Publication Data
US 2013/0129804 A1    May 23, 2013

(30) Foreign Application Priority Data
May 14, 2010    (EP) .................................... 10162814

(51) Int. Cl.
| | |
|---|---|
| *A01N 59/26* | (2006.01) |
| *A01N 59/16* | (2006.01) |
| *A01N 25/00* | (2006.01) |
| *A61K 35/618* | (2015.01) |
| *A01N 37/44* | (2006.01) |

(52) U.S. Cl.
CPC ............... *A01N 25/008* (2013.01); *A01N 37/44* (2013.01); *A01N 59/16* (2013.01); *A01N 59/26* (2013.01)

(58) Field of Classification Search
None
See application file for complete search history.

(56) References Cited

U.S. PATENT DOCUMENTS

| | | | |
|---|---|---|---|
| 6,703,036 B1 * | 3/2004 | Young | .......................... 424/410 |
| 2003/0181332 A1 | 9/2003 | Sedun et al. | |

FOREIGN PATENT DOCUMENTS

| EP | 1402776 A1 † | 3/2004 |
|---|---|---|
| EP | 1402776 B1 | 5/2010 |
| WO | 9939576 A1 | 8/1999 |
| WO | 2009048345 A1 † | 4/2009 |
| WO | WO 2009048345 A1 * | 4/2009 |

OTHER PUBLICATIONS flour nutrition data, http://nutritiondata.self.com/facts/cereal-grains-and-pasta/5745/2#.*
International Search Report for PCT/EP2011/057751, Jan. 2, 2012, 3 pages.
Written Opinion of the International Searching Authority for PCT/EP2011/057751, Jan. 2, 2012, 6 pages.
The translation of the International Preliminary Report on Patentability issued in corresponding international application serial No. PCT/EP2011/057751 (10 pages), 2011.
AkzoNobel Functional Chemicals Chelates: Dissolvine® GL Technical Brochure, pp. 1-16, Apr. 2010.
Akzo Nobel: Dissolvine GL, pp. 1-10, Nov. 2002.

* cited by examiner
† cited by third party

*Primary Examiner* — Misook Yu
*Assistant Examiner* — Kauser M Akhoon
(74) *Attorney, Agent, or Firm* — Saul Ewing LLP; Peter C. Lauro, Esq.

(57) ABSTRACT

The invention relates to bait formulations comprising at least one iron salt, at least one component selected from among methyl glycine-N,N-diacetic acid, glutamine-N,N-diacetic acid, and the alkali metal, alkaline earth metal and ammonium salts thereof; and at least one starch-containing component. The invention also relates to the use of said bait formulation for controlling terrestrial slugs and snails and to a method for controlling terrestrial slugs and snails using the bait formulation of the invention.

14 Claims, No Drawings

BAIT FORMULATIONS FOR CONTROLLING SLUGS AND SNAILS

This application is the U.S. national phase, pursuant to 35 U.S.C. §371, of PCT international application Ser. No. PCT/EP2011/057751, filed May 13, 2011, designating the United States and published on Nov. 17, 2011 as publication WO 2011/141566 A3, which claims priority to European Application Ser. No. 10162814.7, filed May 14, 2010. The entire contents of the aforementioned patent applications are incorporated herein by this reference.

The present invention relates to bait formulations comprising at least one iron salt, at least one component selected from methylglycine-N,N-diacetic acid, glutamine-N,N-diacetic acid, the alkali metal salts, alkaline earth metal salts and ammonium salts thereof; and at least one starch-containing component. The invention also relates to the use of this bait formulation for control of land-dwelling slugs and snails, and to a method for controlling land-dwelling slugs and snails using the inventive bait formulation.

Slugs and snails can be a considerable problem in agriculture and horticulture, and cause high economic damage particularly in rainy years. For instance, many slug and snail species, especially slugs, damage plants to the extent of skeletonization and completely destroy the seasonal harvest. Moreover, slugs and snails are intermediate hosts for many parasites and pathogens. For instance, the amber snail is an intermediate host for the distome *Leucochloridium paradoxum* which infests birds; and some slug species spread plant pathogens. Invasive species are also problematic, such as the Spanish slug (*Arion lusitanicus* or *Arion vulgaris*) introduced from western Europe in the 1970s, which does not have any natural predator in central Europe and displaces native slug and snail species.

Slugs and snails are usually controlled by the use of contact molluscicides or feed molluscicides, and feed poisons, especially in the form of bait formulations, generally have higher efficacy. Customary bait formulations comprise methiocarb, metaldehyde, metal salts such as aluminum sulfate or iron (III) phosphate, or metal chelates such as iron salts of EDTA, and a feedant. Metaldehyde is an effective molluscicide, but is not selective and therefore constitutes, especially when misused, a hazard to other animals, especially vertebrates such as birds and mammals. Methiocarb is also suspected of being toxic to and harming other animals and especially mammals. The metal salts are nontoxic or at least less toxic than methiocarb and metaldehyde but the efficacy thereof is not always satisfactory. The metal chelates based on EDTA have good molluscicidal activity, but EDTA does not have good biodegradability, and is additionally considered to be of ecological concern when deployed to the soil in a relatively large amount, since it can dissolve heavy metals from the soil and make them bioavailable.

WO 96/05728 describes molluscicidal feed bait formulations which comprise, as well as an inert edible carrier, an iron(III) edetate or an iron(III) hydroxyethyl derivative of EDTA, or else a simple iron compound in combination with EDTA or a hydroxyethyl derivative of EDTA. The amounts of EDTA in these formulations are comparatively high and are preferably in the range from 0.7 to 1.7% by weight.

WO 99/38576 describes molluscicidal feed bait formulations which, as well as an inert edible carrier, comprise an iron compound and ethylenediaminedisuccinic acid (EDDS) or a salt thereof. EDDS is comparatively costly.

WO 2009/048345 describes molluscicidal feed bait formulations which, as well as an inert edible carrier, comprise iron powder, i.e. elemental iron, or a pulverulent iron alloy and at least one complexing agent. Preferred complexing agents are EDTA, salts thereof, and mixtures with other complexing agents.

It was an object of the present invention to provide bait formulations with molluscicidal efficacy, which do not have the abovementioned disadvantages of the prior art. More particularly, the bait formulations were to be nontoxic with comparable molluscicidal efficacy and to have better environmental compatibility. As well as the molluscicidal action, the bait formulations should ensure that the slugs and snails rapidly stop their harmful feeding before they die due to the deadly effect of the bait formulation.

These and further objects are achieved by the solid bait formulations described hereinafter.

The invention thus relates to bait formulations in solid form comprising:

a) at least one iron salt, preferably selected from iron salts in which iron is in the +2 or +3 oxidation state, and mixtures thereof;

at least one of components b) and c) defined hereinafter;

b) component b) selected from methylglycine-N,N-diacetic acid, the alkali metal salts, alkaline earth metal salts and ammonium salts thereof, and mixtures thereof;

c) component c) selected from glutamine-N,N-diacetic acid, the alkali metal salts, alkaline earth metal salts and ammonium salts thereof, and mixtures thereof;

and d) at least one starch-containing component.

The inventive bait formulations have high molluscicidal action and reduce feeding damage significantly. Unlike in the prior art, these advantageous effects are also achieved when the inventive formulations do not comprise any EDTA or EDDS or comprise only small amounts thereof, for example at a content of EDTA or EDDS below 2000 ppm, for example a maximum of 1900 ppm, where EDTA and EDDS are each calculated as the free acid and the content is based on the total weight of the bait formulation.

The remarks which follow regarding preferred configurations of the inventive bait formulations, especially regarding preferred configurations of the components a) to d) present therein, of further optional components and of the weight ratios thereof apply either taken alone or in any conceivable combination with one another. Here and hereinafter, the terms "formulation" and "bait formulation" are used synonymously.

Useful iron salts are in principle all iron salts and hydrates thereof which are approved for use in bait formulations and which are known to have molluscicidal action. The iron salts may comprise either di- or trivalent iron, i.e. the iron salts are salts in which iron is in the +2 oxidation state or in the +3 oxidation state, or mixtures thereof. Suitable iron salts are, for example, iron(II) sulfate, iron(II) phosphate, iron(III) pyrophosphate, iron(III) orthophosphate, iron(III) citrate, iron(II) edetate, iron(III) edetate, iron(III) oxide, iron(III) albuminate, iron(III) chloride, iron(II) gluconate, iron(II) lactate, iron (III) nitrate, iron(II) stearate, iron(III) stearate, iron(III) tartrate, iron fumarate, iron proteins, iron carbohydrates such as iron gluconate, where the aforementioned salts may be in anhydrous form or the hydrate form. Also suitable are mixtures of the aforementioned salts. Preference is given among these to iron(II) sulfate, iron(III) phosphate, iron(III) citrate, iron(II) edetate and iron(III) edetate, and the hydrates of the aforementioned iron salts and mixtures thereof, even greater preference being given to iron(II) sulfate and iron(III) phosphate and the hydrates and mixtures thereof. Particular preference is given to using, as component a), a finely divided iron salt having a mean primary particle size of <1 μm, especially <0.5 μm, for example in the range from 0.02 to <1 μm, especially in the range from 0.03 to 0.5 μm (determined visually by means of scanning electron microscopy). Specifically, component a) used is iron(III) orthophosphate. Particular preference is given to using, as component a), a finely divided iron(III) orthophosphate having a mean primary particle size of <1 μm, especially <0.5 μm, for example in the range from 0.02 to <1 μm, especially in the range from 0.03 to 0.5 μm (determined visually by means of scanning electron microscopy). Such iron(III) orthophosphates are known, for example, from WO 2009/050055 or WO 2008/009592.

The iron salts are present in the bait formulations in a total amount of preferably 0.01 to 5% by weight, more preferably 0.1 to 3% by weight, particularly of 0.1 to 1.5% by weight, especially of 0.1 to 0.9% by weight, based on iron (i.e. the anion is not taken into account in this calculation) and based on the total weight of the bait formulation.

In a preferred embodiment, the inventive bait formulations comprise component b), i.e. methylglycine-N,N-diacetic acid (synonym: alanine-N,N-diacetic acid; MGDA) and/or an alkali metal salt, alkaline earth metal salt or ammonium salt thereof, or one of these salts or a mixture of MGDA with one or more of its salts. MGDA has the following structure:

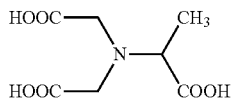

and may be present in the inventive formulations either as the free acid or as the alkali metal salt, alkaline earth metal salt or ammonium salt thereof, or mixtures of the acid with the salts, or as mixtures of the salts of MGDA. MGDA may be used in the inventive formulations either in the L form or in the D form, or in the form of mixtures of D and L forms, for example in the form of the racemate thereof. Typically, MGDA is used in the form of the racemate thereof.

Suitable alkali metal salts of MGDA are, for example, the lithium, sodium and potassium salts, preference being given to the sodium and potassium salts. Suitable alkaline earth metal salts of MGDA are, for example, the magnesium and calcium salts. Among the salts of MGDA, preference is given to the alkali metal salts and especially to the sodium and potassium salts.

The salts of MGDA may be the monosalts, disalts or trisalts, or else mixed forms thereof, i.e. MGDA may be present in various degrees of partial neutralization or in fully neutralized form. In addition, the salts may be homogeneous or mixed. Homogeneous salts are understood to mean those salts which comprise only one of the cations mentioned, while various cations among those mentioned are present in mixed salts.

Preference is given to using, as component b), MGDA in the form of one of its sodium salts, especially in the form of the trisodium salt.

Component b) is present in the bait formulations generally in a total amount of 0.05 to 10% by weight, preferably 0.1 to 5% by weight, especially from 0.2 to 3% by weight, more preferably from 0.2 to 1.8% by weight and most preferably from 0.3 to 1.5% by weight, based on the free acid (i.e. any countercation(s) present are not taken into account in this calculation) and based on the total weight of the bait formulation.

In another embodiment, the inventive formulations comprise not only components a), optionally b) and d) but also component c), namely glutamine-N,N-diacetic acid and/or an alkali metal salt, alkaline earth metal salt or ammonium salt thereof. Glutamine-N,N-diacetic acid (GLDA) has the following structure

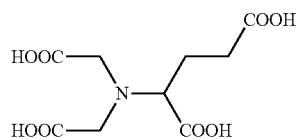 [SMILES: O=C(O)CCC(C(=O)O)N(CC(=O)O)CC(=O)O]

and may be present in the inventive formulation either as the free acid or as an alkali metal salt, alkaline earth metal salt or ammonium salt thereof, or mixtures of the acid with the salts or as mixtures of the salts of GLDA. In the inventive formulations, GLDA may be used either in the L form or in the D form, or in the form of mixtures of the D and L forms, for example in the form of its racemate. Typically, GLDA is used in the form of its racemate.

Suitable alkali metal salts of GLDA are, for example, the lithium, sodium and potassium salts, preference being given to the sodium and potassium salts. Suitable alkaline earth metal salts of GLDA are, for example, the magnesium and calcium salts. Among the salts of GLDA, the alkali metal salts and especially the sodium and potassium salts are preferred.

The salts of GLDA may be the monosalts, disalts, trisalts or tetrasalts, or else mixed forms thereof, i.e. GLDA may be present in different degrees of partial neutralization or in fully neutralized form. In addition, the salts may be homogeneous or mixed. Homogeneous salts are understood to mean those salts which comprise only one of the cations mentioned, while various cations among those mentioned are present in mixed salts.

Preference is given to using, as component c), GLDA in the form of the tetrasodium salt.

If present, glutamine-N,N-diacetic acid or the alkali metal salt, alkaline earth metal salt or ammonium salt thereof is present in the inventive formulations in a concentration of generally 0.01 to 2.5% by weight, preferably 0.05 to 2% by weight, particularly of 0.1 to 1.5% by weight and especially of 0.1 to 1% by weight, calculated as the free acid and based on the total weight of the bait formulation.

In a particularly preferred embodiment, the inventive bait formulations comprise component b), and especially both component b) and component c), i.e. a combination of MGDA and/or one of its salts and GLDA and/or one of its salts, the salts of GLDA and of MGDA being selected from their alkali metal salts, alkaline earth metal salts and ammonium salts. In this embodiment, the inventive formulation comprises GLDA and MGDA or salts thereof in such an amount that the weight ratio of the total amount of GLDA or the alkali metal or alkaline earth metal salt thereof to the total amount of MGDA or the alkali metal or alkaline earth metal salt thereof is preferably in the range from 1:0.3 to 1:20, especially preferably from 1:0.4 to 1:15, more preferably from 1:0.5 to 1:10, even more preferably from 1:0.8 to 1:10 and especially from 1:1 to 1:10, based in each case on the free acids.

In another particularly preferred embodiment, the inventive bait formulations comprise component b) without component c), i.e. MGDA and/or one of the salts thereof and no GLDA or none of the salts of GLDA.

"Based on the free acids" and "calculated as the free acid" mean, in connection with GLDA and MGDA, that any countercation(s) present is not taken into account in the calculation of the concentration or of the weight ratio of MGDA to GLDA.

Preference is given especially to inventive bait formulations which comprise component b) and component c). In these preferred bait formulations, glutamine-N,N-diacetic acid and/or an alkali metal salt, alkaline earth metal salt or ammonium salt thereof is present in a concentration of 0.01 to 2.5% by weight, preferably 0.05 to 2% by weight, particularly from 0.1 to 1.5% by weight and especially from 0.1 to 1% by weight, calculated as the free acid and based on the total weight of the bait formulation, where the total concentration of glutamine-N,N-diacetic acid and methylglycine-N,N-diacetic acid, calculated as the free acid and based on the total weight of the bait formulation, is preferably in the range from 0.1 to 10% by weight, especially in the range from 0.2 to 5% by weight, more preferably in the range from 0.2 to 3% by weight, even more preferably in the range from 0.2 to 1.8% by weight and especially in the range of 0.3 to 1.5% by weight.

The inventive formulation more preferably comprises glutamine-N,N-diacetic acid and/or an alkali metal salt, alkaline earth metal salt or ammonium salt thereof in a concentration of 0.01 to 2% by weight and especially of 0.1 to 1% by weight, calculated as the free acid, where the total concentration of glutamine-N,N-diacetic acid and methylglycine-N,N-diacetic acid, calculated as the free acid and based on the total weight of the bait formulation, is in the range from 0.1 to 10% by weight, preferably 0.11 to 5% by weight or 0.2 to 5% by weight, more preferably in the range from 0.2 to 3% by weight, even more preferably in the range from 0.2 to 1.8% by weight and especially in the range of 0.3 to 1.5% by weight.

The inventive bait formulation further comprises a starch-containing substance as component d). The starch-containing component d) may be any desired starch-containing product which is edible and non-repellent to slugs and snails. Examples of suitable starch-containing substances as component d) are flours such as cereal flours, e.g. wheat flour, corn flour, millet flour, rye flour, triticale flour, oat flour and barley flour, rice flour or potato flour, bran, breadcrumbs, seeds, seed parts, starch obtained from potato flour, cereal flour or rice flour, and mixtures thereof. Preference is given among these to cereal flours, rice flour and mixtures thereof. Preferred cereal flours are wheat flour, triticale flour and corn flour, greater preference being given to wheat flour (both hard and soft wheat flour). More particularly, the starch-containing component d) comprises wheat flour and especially soft wheat flour. If component d) is particulate, it is preferably in finely divided form, preferably in particle sizes of at most 250 μm and especially of at most 180 μm, determined by sieve analysis.

If flour is used as component d), it is preferably in finely divided form, preferably in particle sizes of at most 250 μm and especially of at most 180 μm.

The starch-containing substance is present in the inventive formulation generally in an amount of 60 to 99.89% by weight, preferably from 70 to 99.85% by weight, especially from 75 to 99.8% by weight, more preferably from 75 to 99% by weight, based on the total weight of the bait formulation.

In a further preferred embodiment, the inventive formulations comprise, in addition to components b) and/or c), especially in combination with component b) or in combination with a mixture of components b) and c), e1) ethylene-1,2-diamino-N,N,N',N'-tetraacetic acid (EDTA) and/or a salt thereof (component e1), generally in an amount of not more than 0.19% by weight, for example in an amount of 0.01 to 0.19% by weight, preferably in an amount of 0.03 to 0.18% by weight and especially in an amount of 0.05 to 0.15% by weight, based on the free acid and based on the total weight of the bait formulation.

"Calculated as/based on the free acid" means that any countercation(s) present are not taken into account in this calculation.

EDTA may be present in the inventive formulation either as the free acid or as a salt, for example as an alkali metal salt, alkaline earth metal salt, ammonium salt, iron salt or iron complex, or mixtures of the acid with the salts, or as mixtures of the salts of EDTA.

Suitable alkali metal salts are, for example, the lithium, sodium and potassium salts, preference being given to the sodium and potassium salts. Suitable alkaline earth metal salts are, for example, the magnesium and calcium salts. Suitable iron salts or complexes are iron(II) edetate and iron (III) edetate. Among the salts, preference is given to the alkali metal salts and especially the sodium and potassium salts, specifically the sodium salts.

The salts may be the monosalts, disalts, trisalts or tetrasalts, or else mixed forms thereof, i.e. EDTA may be present in different degrees of partial neutralization or in fully neutralized form. In addition, the salts may be homogeneous or mixed. Homogeneous salts are understood to means those salts which comprise only one of the cations mentioned, whereas various cations among those mentioned are present in mixed salts.

Preference is given to using, as component e1), EDTA in the form of the free acid or in the form of the iron complex, such as Fe(II) edetate or Fe(III) edetate.

Preferably, however, the concentration of EDTA, whether in the form of the free acid or in the form of a salt or complex thereof, in the inventive formulations will not exceed a value of 0.19% by weight, especially of 0.15% by weight, calculated as the free acid and based on the total weight of the bait formulation.

In a further preferred embodiment, the inventive formulations comprise, in addition to components b) and/or c), especially in combination with component b) or in combination with a mixture of components b) and c), e2) ethylenediaminodisuccinic acid (EDDS) and/or salt thereof (component e2) in an amount of generally not more than 0.19% by weight, for example in an amount of 0.01 to 0.19% by weight, preferably from 0.03 to 0.18% by weight and especially from 0.05 to 0.15% by weight, based on the free acid and based on the total weight of the bait formulation.

"Calculated as/based on the free acid" means that any counter cation(s) present are not taken into account in this calculation.

EDDS may be present in the inventive bait formulations either as the free acid or as a salt, for example as an alkali metal salt, alkaline earth metal salt, ammonium salt, iron salt or iron complex, or mixtures of the acid with the salts or as mixtures of the salts of EDDS. EDDS itself has two centers of asymmetry in the molecule and may therefore be present in the form of a diastereomer mixture or in the form of the pure diastereomers, for example in the form of the S,S enantiomer, of the R,R enantiomer or of the R,S diastereomer.

Suitable alkali metal salts are, for example, lithium, sodium and potassium salts, preference being given to the sodium and potassium salts. Suitable alkali earth metal salts are, for example, the magnesium and calcium salts. Suitable iron salts or complexes are iron(II) EDDS and iron(III) EDDS. Among the salts, preference is given to the alkali metal salts and especially the sodium and potassium salts, specifically the sodium salts.

The salts may be the monosalts, disalts, trisalts or tetrasalts, or else mixed forms thereof, i.e. EDDS may be present in various degrees of partial neutralization or in the fully neutralized form. In addition, the salts may be homogeneous or mixed. Homogeneous salts are understood to mean salts which comprise only one of the cations mentioned, whereas various cations among those mentioned are present in mixed salts.

Preference is given to using, as component e2), EDDS in the form of the free acid, in the form of the trisodium salt or in the form of an iron complex such as Fe(II) EDDS or Fe(III) EDDS.

Preferably, however, the concentration of EDDS, whether in the form of the free acid or in the form of a salt or complex thereof, in the inventive formulations will not exceed a value of 0.19% by weight, especially of 0.15% by weight, calculated as the free acid and based on the total weight of the bait formulation.

In a preferred embodiment of the invention, the bait formulation comprises not only components a), b) and/or c) and d) but also component e1).

In a further preferred embodiment of the invention, the bait formulation comprises not only components a), b) and/or c) and d) but also component e2).

In a further preferred embodiment of the invention, the bait formulation comprises not only components a), b) and/or c) and d) but also components e1) and e2). In this embodiment, the ratio of e1) and e2) (weight ratio of EDTA to EDDS, in each case calculated as the free acid) is preferably in the range from 1:20 to 20:1, especially in the range from 1:10 to 10:1. The total concentration of component e1)+component e2) will generally not exceed 0.3% by weight and especially 0.19% by weight or 0.15% by weight, calculated in each case as the free acid and based on the total weight of the bait formulation, and is, for example, in the range from 0.01 to 0.3% by weight, frequently in the range from 0.02 to 0.19% by weight, preferably in the range from 0.03 to 0.18% by weight and especially in the range from 0.05 to 0.15% by weight, based on the free acid and based on the total weight of the bait formulation.

In a further preferred embodiment of the invention, the bait formulations, aside from components a), b) and/or c) and d), do not comprise any of components e1) and e2).

In a further preferred embodiment of the invention, the bait formulations comprise:
a) 0.01 to 5% by weight, preferably 0.1 to 3% by weight, particularly 0.1 to 1.5% by weight, especially 0.1 to 0.9% by weight, based on the total weight of the bait formulation, of iron in the form of the at least one iron salt;
b) 0.1 to 5% by weight, especially 0.2 to 3% by weight, more preferably 0.2 to 1.8% by weight and most preferably 0.3 to 1.5% by weight, based on the total weight of the bait formulation, of component b);
c) optionally 0.01 to 2.5% by weight, preferably 0.05 to 2% by weight, particularly 0.1 to 1.5% by weight and especially 0.1 to 1% by weight, based on the total weight of the bait formulation, of component c);
   where the total concentration of component b) and component c), calculated in each case as the free acid and based on the total weight of the bait formulation, is in the range from 0.11 to 5% by weight or 0.2 to 5% by weight, more preferably in the range from 0.2 to 3% by weight or 0.3 to 3% by weight, even more preferably in the range from 0.2 to 1.8% by weight or 0.3 to 1.8% by weight and especially in the range of 0.3 to 1.5% by weight or 0.4 to 1.5% by weight;
d) 60 to 99.89% by weight, preferably 70 to 99.85% by weight, especially 75 to 99.8% by weight, more preferably 75 to 99.5% by weight or 75 to 99% by weight, based on the total weight of the bait formulation, of at least one starch-containing component.

In a further preferred embodiment of the invention, the bait formulations comprise:
a) 0.01 to 5% by weight, preferably 0.1 to 3% by weight, particularly 0.1 to 1.5% by weight, especially 0.1 to 0.9% by weight, based on the total weight of the bait formulation, of iron in the form of the at least one iron salt;
b) 0.1 to 5% by weight, especially 0.2 to 3% by weight, more preferably 0.2 to 1.8% by weight and most preferably 0.3 to 1.5% by weight, based on the total weight of the bait formulation, of component b);
c) optionally 0.01 to 2.5% by weight, preferably 0.05 to 2% by weight, particularly 0.1 to 1.5% by weight and especially 0.1 to 1% by weight, based on the total weight of the bait formulation, of component c);
   where the total concentration of component b) and component c), calculated in each case as the free acid and based on the total weight of the bait formulation, is in the range from 0.11 to 5% by weight or 0.2 to 5% by weight, more preferably in the range from 0.2 to 3% by weight or 0.3 to 3% by weight, even more preferably in the range from 0.2 to 1.8% by weight or 0.3 to 1.8% by weight and especially in the range of 0.3 to 1.5% by weight or 0.4 to 1.5% by weight;
d) 60 to 99.89% by weight, preferably 70 to 99.85% by weight, especially 75 to 99.8% by weight, more preferably 75 to 99.5% by weight or 75 to 99% by weight, based on the total weight of the bait formulation, of at least one starch-containing component;
e1) 0.01 to 0.19% by weight, preferably from 0.03 to 0.18% by weight and especially from 0.05 to 0.15% by weight of EDTA or a salt thereof, where the EDTA content is based on the free acid and on the total weight of the bait formulation.

In a further preferred embodiment of the invention, the bait formulations comprise:
a) 0.01 to 5% by weight, preferably 0.1 to 3% by weight, particularly 0.1 to 1,5% by weight, especially 0.1 to 0.9% by weight, based on the total weight of the bait formulation, of iron in the form of the at least one iron salt;
b) 0.1 to 5% by weight, especially 0.2 to 3% by weight, more preferably 0.2 to 1.8% by weight and most preferably 0.3 to 1.5% by weight, based on the total weight of the bait formulation, of component b);
c) optionally 0.01 to 2.5% by weight, preferably 0.05 to 2% by weight, particularly 0.1 to 1.5% by weight and especially 0.1 to 1% by weight, based on the total weight of the bait formulation, of component c);
   where the total concentration of component b) and component c), calculated in each case as the free acid and based on the total weight of the bait formulation, is in the range from 0.11 to 5% by weight or 0.2 to 5% by weight, more preferably in the range from 0.2 to 3% by weight or 0.3 to 3% by weight, even more preferably in the range from 0.2 to 1.8% by weight or 0.3 to 1.8% by weight and especially in the range of 0.3 to 1.5% by weight or 0.4 to 1.5% by weight;
d) 60 to 99.89% by weight, preferably 70 to 99.85% by weight, especially 75 to 99.8% by weight, more preferably 75 to 99.5% by weight or 75 to 99% by weight, based on the total weight of the bait formulation, of at least one starch-containing component;

e2) 0.01 to 0.19% by weight, preferably from 0.03 to 0.18% by weight and especially from 0.05 to 0.15% by weight of EDDS or a salt thereof, where the EDDS content is based on the free acid and on the total weight of the bait formulation.

As well as the aforementioned constituents, the inventive bait formulations may also comprise further constituents which may be present in bait formulations. These include especially protein-containing substances (component f), glucose and glucose-containing disaccharides (component g), comminuted seeds of oil plants (component h) and other conventional formulation constituents such as binders, preservatives, dyes, slug and snail attractants, lubricants, water repellents, grinding aids, additives, bitter substances, homeotherm repellents and/or anticaking agents, and also further molluscicidal active ingredients. The total amount of these constituents will generally not exceed 30% by weight and especially 20% by weight, based on the total weight of the formulation, and is typically in the range from 2 to 30% by weight and especially in the range from 2.5 to 20% by weight.

In a further preferred embodiment, the inventive bait formulations comprise, in addition to the aforementioned components a), b) and/or c), d) and optionally e1) and/or e2), at least one protein-containing substance as component f).

Preferred protein-containing substances are, for example, casein, egg white powder, egg powder, fish meal, meat meal, blood meal, protein hydrolyzates and mixtures thereof.

The at least one protein-containing substance is present in the inventive bait formulations generally in an amount of 1 to 10% by weight, preferably 1 to 7% by weight and especially 1 to 5% by weight, based on the total weight of the bait formulation.

In a further preferred embodiment, the inventive bait formulations comprise, in addition to the aforementioned components a), b) and/or c), d), optionally e1) and/or e2) and optionally f), glucose and/or a glucose-containing disaccharide as component g).

Suitable glucose-containing disaccharides are, for example, sucrose, maltose, isomaltose, isomaltulose, trehalose or lactose, preference being given to sucrose.

Glucose and/or the glucose-containing disaccharide are present in the inventive formulations in a total amount of, for example, 1 to 10% by weight, preferably 1 to 5% by weight and especially 1 to 3% by weight, based on the total weight of the bait formulation.

As well as the aforementioned constituents, the inventive formulations may also comprise comminuted, for example ground or kibbled, seeds of oil plants (component h). These include, for example, seeds from oilseed rape, turnip rape, mustard, oil radish, camelina, rocket, crambe, sunflower, safflower, thistle, calendula, soybean, lupin, flax, hemp, oil pumpkin, poppy, corn and nuts such as peanuts. If present, the amount of comminuted oil plant seeds will not exceed 5% by weight, especially 3% by weight, and will, for example, be 0.1 to 5% by weight or 0.2 to 3% by weight. In a preferred embodiment, the formulation comprises less than 0.1% by weight, if any, based on the bait formulation, of comminuted seeds of oil plants.

The inventive bait formulations may also comprise further constituents, for example binders, preservatives, dyes, slug and snail attractants, lubricants, water repellents, grinding aids, additives, bitter substances, homeotherm repellents and/or anticaking agents, and also further molluscicidal active ingredients. The total amount of further constituents, i.e. of constituents other than components a) to h), will generally not be more than 10% by weight, based on the total weight of the formulation, and is frequently in the range from 0.1 to 10% by weight, based on the total weight of the formulation.

Suitable binders are, for example, modified starch, formaldehyde-releasing substances, polyvinyl alcohol, optionally partly hydrolyzed polyvinyl acetate, and molasses.

Modified starches are chemically or physically processed starches which satisfy increased technical demands and have, for example, better heat stability, acid stability, shear stability, better swellability, improved flow characteristics and better freeze and thaw characteristics. They are produced, for example, by the treatment of natural starch with acids or bases, by oxidation, enzymatic treatment, phosphation, acetylation, by heat and/or pressure treatment, and many others. A preferred modified starch is cold-swelling corn starch.

The formaldehyde-releasing substances present may be any customary products suitable for release of formaldehyde. Preference is given to urea-formaldehyde condensation products.

Useful polyvinyl alcohols and polyvinyl acetates which may be present in partly hydrolyzed form preferably include the products known by the Mowilith (from Clariant) and Mowiol (from Clariant) trade names.

Molasses are understood in the present case to mean customary syrupy mother liquors obtained in the manufacture of sugar.

Useful preservatives include all customary substances suitable for this purpose. Examples include 2-hydroxybiphenyl, sorbic acid and salts thereof such as potassium sorbafe, p-hydroxybenzaldehyde, methyl p-hydroxybenzoate, benzaldehyde, benzoic acid and salts thereof such as sodium benzoate, propyl p-hydroxybenzoate, natamycin and p-nitrophenol. Such preservatives are used typically in an amount of 0.01 to 0.5% by weight, based on the total weight of the bait formulation.

Useful dyes include all customary substances suitable for this purpose. Examples include inorganic pigments such as iron oxide, titanium dioxide and ferrocyanine blue, and organic dyes such as anthraquinone, azo and metal phthalocyanine dyes. Such dyes are typically used in an amount of 0.001 to 0.1% by weight, based on the total weight of the bait formulation.

Useful slug and snail attractants include all customary substances suitable for this purpose. The examples include plant extracts and the conversion products thereof, and products of animal origin, for example banana extract or yeasts, particularly brewer's yeasts.

Useful additives include substances suitable to adjusting the pH in the bait formulations. One example is citric acid.

Useful grinding aids include all substances suitable for this purpose. Examples include kaolins, aluminas, talc, chalk, ground quartz and finely divided silica.

Useful lubricants typically include stearates such as magnesium stearate, or phyllosilicates such as talc. Such lubricants are used typically in an amount of 0.5 to 8% by weight, based on the total weight of the bait formulation.

As water repellents come, for example, waxes or waxy substances, such as synthetic waxes such as paraffin wax, Fischer-Tropsch waxes, polyethylene waxes, animal waxes such as beeswax or wool wax, vegetable waxes such as sugarcane wax, candelilla wax or carnauba wax, and mineral wax such as ozocerite. Such water repellents are typically used in an amount of 0.5 to 8% by weight, based on the total weight of the bait formulation.

Useful homeotherm repellents which exert a repellent effect on warm-blooded life forms, such as dogs or hedgehogs, include all substances customary for this purpose. One example is N-vanillylnonanamide.

Useful bitter substances are all substances customary for this purpose. One example is denatonium benzoate.

Useful anticaking agents include all substances which are customary for this purpose and prevent lump formation and caking. Examples include moisture-adsorbing powders such as kieselguhr, fumed silicas, tricalcium phosphate, calcium silicates, aluminum oxide, magnesium oxide, magnesium carbonate, zinc oxide, stearates and fatty amines.

Useful additional molluscicidal active ingredients include all substances suitable for this purpose. Examples include methiocarb, metaldehyde and metal salts, optionally in a mixture with complexing agents, examples of which include chelates of ethylenediaminetetracetic acid and iron and/or copper ions. The inventive formulation, however, preferably does not comprise any further molluscicidal active ingredients. In a preferred embodiment, the formulation comprises none or less than 0.2% by weight, based on the formulation, of such further molluscicidal active ingredients.

When dispersed in water in an amount of 100 g/l, the inventive bait formulations lead to a pH of the water in the range from preferably 4 to 10, more preferably 4 to 9.5 (determined to CIPAC MT 75), since a higher pH if anything has a repulsive effect on most slug and snail types. When MGDA, GLDA and/or EDTA are used in the form of their salts, it may additionally be necessary to use an acid to achieve the abovementioned pH values. Especially suitable are acids which are solid at room temperature and do not have a repellent effect on the slugs and snails in the amounts used, for example citric acid, malic acid, lactic acid and the like.

The inventive solid formulation is preferably in the form of particles. The particles preferably have a mean dimension in the range from 0.5 to 6 mm, more preferably from 1 to 6 mm and especially from 2 to 6 mm. The mean dimension relates to the averaged values of the longest particle dimension. The mean dimension can be determined in a manner known per se.

The inventive formulation can be produced by customary processes for producing solid slug and snail bait formulations, as described, for example, in WO 03/069996, EP-A-1992226, WO 99/39576 or WO 96/05728. For example, all abovementioned components can be mixed simultaneously or successively with a diluent such as water or an inert organic solvent and processed to give a paste, or the abovementioned components can first be dry-mixed with one another and only then processed with the aid of water or an inert organic solvent to give a paste, and extruded or ground, and the extrudate or ground material can be dried to the desired moisture content and comminuted.

The inventive formulations serve to control terrestrial, i.e. land-dwelling, slugs and snails. The inventive formulations probably act as feed bait, i.e. the slugs and snails consume the bait and the toxic effect unfolds in the digestive tract of the slugs and snails.

The invention therefore further provides for the use of the inventive bait formulation for control of terrestrial slugs and snails, and also a process for control of terrestrial slugs and snails wherein at least one inventive bait formulation is deployed in the habitat of the slugs and snails.

Terrestrial or land-dwelling slugs and snails belong to the subclass of the Pulmonata.

The slugs and snails to be controlled in accordance with the invention include all land-dwelling slugs and snails, the majority of which occur as polyphagus pests in agricultural and horticultural crops. Agriculturally and horticulturally problematic slug and snail types are, for example, slugs such as *Arion rufus* (red slug), *Arion ater, Arion lusitanicus* and other Arionidae, for example *Arion* spp., *Arion subfuscus, Arion circumscriptus* and *Arion hortensis, Limax* species such as *Limax maximus, L. flavus, Limax glavus, Limax tenellus* and *Limax poirieri*, and field slugs such as *Deroceras reticulatum* and *Deroceras agreste* from the Limacidae family, and species from the Milacidae family such as *Milax gagates*, and also harmful snails such as those of the *Cepaea* genus, for example *Cepaea nemoratis* and *Cepaea* spp., *Discus, Helicigona* and *Helicella*.

Particularly problematic are the grey field slug (*Deroceras reticulatum*) and the Spanish slug (*Arion lusitanicus*).

The slugs and snails are controlled by customary methods, for example by deploying the inventive formulation in the habitat of the slugs and snails to be controlled, for example by scattering and/or drilling.

In the control of slugs and snails, the application rate of the inventive formulation can be varied within a relatively wide range. Preference is given to using 2 to 60 kg of formulation per hectare, more preferably 10 to 50 kg per hectare.

The inventive formulation has a comparable molluscicidal efficacy to the bait molluscicides of the prior art, but is non-toxic to vertebrates and also does not have the environmental metal problems with pure EDTA formulations, since it contains at most only minor amounts, if any, of this complexing agent. More particularly, a molluscicidal activity comparable to the prior art and effective prevention of feeding damage are achieved even in the case of low iron contents.

The invention is illustrated by the nonlimiting examples which follow.

EXAMPLES

Example Formulations

For the studies which follow, the following base formulation was used:

GLDA, MGDA and/or EDTA in the amounts specified in Table 1
Iron salt in the amounts specified in Table 1
Ground linseed 1.0% by weight
Egg white powder 4.0% by weight
Sucrose 2.5% by weight
Additionally:
0.2% by weight of preservative (0.1% by weight of potassium sorbate and 0.1% by weight of a commercial natamycin formulation: Delvocid®)
0.01% by weight of dye
3.0% by weight of magnesium stearate
3.0% by weight of paraffin wax
Wheat flour ad 100%

Production of the Formulations

Wheat flour was mixed with ground linseed. Egg white powder was mixed with sucrose, iron salt and components b), c) and e), and ground briefly in a laboratory mill. 15 grams of water were added to 100 grams of solid mixture and the mixture was stirred intimately. Lubricant, wax, dye and preservative were added, and the whole mixture was mixed and extruded with a laboratory extruder to give a strand, comminuted and dried.

TABLE 1

| Formulation No. | Active constituent [1] [2] | | |
|---|---|---|---|
| 1A | Fe: | 3630 ppm, as iron(III) phosphate |
|    | MGDA: | 9640 ppm, as trisodium salt: |
| 2A | Fe: | 3630 ppm, as iron(III) phosphate |

TABLE 1-continued

| Formulation No. | Active constituent [1) 2)] | |
|---|---|---|
| | MGDA: | 11570 ppm as trisodium salt |
| 3A | Fe: | 7260 ppm as iron(III) phosphate |
| | MGDA: | 23140 ppm, as trisodium salt: |
| 1B | Fe: | 3630 ppm, as iron(III) phosphate |
| | GLDA: | 9830 ppm, as tetrasodium salt |
| 2B | Fe: | 3015, as iron(II) sulfate |
| | GLDA: | 9830 ppm, as tetrasodium salt |
| 1C (noninventive) | Fe: | 1300 ppm, as iron(III) phosphate |
| | EDTA: | 1000 ppm, as disodium salt |
| 2C (noninventive) | Fe: | 3630 ppm, as iron(III) phosphate |
| | EDTA: | 1000 ppm, as disodium salt |
| 3C (noninventive) | Fe: | 3630 ppm, as iron(III) phosphate |
| | EDTA: | 1000 ppm, as the free acid |
| 1D | Fe: | 3630 ppm, as iron(III) phosphate |
| | MGDA: | 9640 ppm, as trisodium salt |
| | GLDA: | 1092 ppm, as tetrasodium salt |
| 2D | Fe: | 3630 ppm, as iron(III) phosphate |
| | MGDA: | 9640 ppm, as trisodium salt |
| | GLDA: | 2730 ppm, as tetrasodium salt |
| 3D | Fe: | 3630 ppm, as iron(III) phosphate |
| | MGDA: | 9640 ppm, as trisodium salt |
| | GLDA: | 8190 ppm, as tetrasodium salt |
| 5D | Fe: | 3630 ppm, as iron(III) phosphate |
| | MGDA: | 6426 ppm, as trisodium salt |
| | GLDA: | 7400 ppm, as tetrasodium salt |
| 6D | Fe: | 3015, as iron(II) sulfate |
| | MGDA: | 6426 ppm, as trisodium salt |
| | GLDA: | 7400 ppm, as tetrasodium salt |
| 1E | Fe: | 1300 ppm, as iron(III) phosphate |
| | MGDA: | 12852 ppm, as trisodium salt |
| | EDTA: | 1000 ppm, as disodium salt |
| 2E | Fe: | 3630 ppm, as iron(III) phosphate |
| | MGDA: | 16065 ppm, as trisodium salt |
| | EDTA: | 1000 ppm, as the free acid |
| 3E | Fe: | 3630 ppm, as iron(III) phosphate |
| | MGDA: | 19278 ppm, as trisodium salt |
| | EDTA: | 1000 ppm, as the free acid |
| 4E | Fe: | 4533 ppm, as iron(III) phosphate [3)] |
| | MGDA: | 19278 ppm, as trisodium salt |
| | EDTA: | 1000 ppm, as the free acid |
| 5E | Fe: | 4630 ppm, as iron(III) phosphate [3)] |
| | MGDA: | 6800 ppm, as trisodium salt |
| | EDTA: | 900 ppm, as the free acid |
| 1F | Fe: | 3630 ppm, as iron(III) phosphate |
| | MGDA: | 16065 ppm, as trisodium salt |
| | GLDA: | 2730 ppm, as tetrasodium salt |
| | EDTA: | 1000 ppm, as the free add |

[1)] The specified amount of iron is based on pure iron without a counterion.
[2)] The specified amount of GLDA, MGDA or EDTA is based in each case on the free acid.
[3)] The iron phosphate used was a nanofine iron phosphate having a primary particle size of <1 μm.

Study of Molluscicidal Action:

The invention formulations were tested for their molluscicidal action both in laboratory experiments and in field experiments.

1. Laboratory Experiments:

The efficacy experiments were conducted in 17 cm×12 cm×6 cm plastic trays each containing 3 or 5 slugs of the *Arion* spp. or *Deroceras* spp. genera. The bottom of each tray was covered with wet filter paper, and the trays were closed with transparent plastic lids containing small air holes. 2 g in each case of the formulations were placed into a glass Petri dish (diameter 3-5 cm, height 0.7-1.0 cm), as was a head of lettuce which was replaced on weekdays. The experiments were conducted under normal daylight conditions in a laboratory.

Table 2 below shows the slug mortality (slugs killed/slugs used) after x days (DAT), and also the bait consumption and the feeding damage in percent.

TABLE 2

| Formulation | Slug species | Dead/used | DAT | Bait consumed | Feeding damage |
|---|---|---|---|---|---|
| 1A | Arion rufus | 3/3 | 5 | 81% | 30% |
| 2A | Arion rufus | 5/5 | 7 | 76% | 10% |
| 3A | Arion rufus | 4/5 | 14 | 70% | 10% |
| 3A | Deroceras reticulatum | 3/3 | 6 | <10% 30 grains distributed | 0 |
| 1B | Arion rufus | 3/5 | 14 | 100% | 30% |
| 1B | Deroceras reticulatum | 2/5 | 14 | <10% 30 grains distributed | 1% |
| 2B | Deroceras reticulatum | 4/5 | 14 | <10% 30 grains distributed | 1% |
| 1C[1)] | Arion rufus | 0/3 | 14 | 90% | 85% |
| 2C[1)] | Arion lusitanicus | 0/3 | 14 | 50% | 50% |
| 3C[1)] | Arion lusitanicus | 0/5 | 14 | 100% | 100% |
| 1D | Arion lusitanicus | 5/5 | 12 | 81% | 0% |
| 2D | Arion lusitanicus | 4/5 | 12 | 62% | 0% |
| 3D | Arion lusitanicus | 5/5 | 12 | 36% | 0% |
| 5D | Arion rufus | 4/5 | 12 | 100% | 30% |
| 5D | Deroceras reticulatum | 4/5 | 14 | <10% 30 grains distributed | 1% |
| 6D | Arion lusitanicus | 3/5 | 12 | 81% | 5% |
| 1E | Arion rufus | 4/5 [3)] | 8 | 30% | 0% |
| 2E | Arion lusitanicus | 3/3 | 6 | 20% | 25% |
| 3E | Arion lusitanicus | 3/3 | 6 | 30% | 10% |
| 3E | Arion rufus | 5/5 | 4 | 95% | 0% |
| 4E | Arion lusitanicus | 5/5 | 4 | 90% | 0% |
| 5E | Deroceras reticulatum | 10/10 | 14 | <10% | 0% |
| 5E | Arion lusitanicus | 5/5 | 4 | 85% | 0% |
| 1F | Arion lusitanicus | 3/3 | 5 | 70% | 0% |
| Biomol ® [2)] | Arion rufus | 0/3 | 14 | 5% | 60% |

[1)] noninventive
[2)] Biomol ® slug pellets, trademark of Bayer CropScience Deutschland GmbH, Langenfeld/Germany
[3)] one slug disappeared 2. Field Experiment The experiment was conducted in a greenhouse according to GEP (Good Experimental Practice) and observing the EPPO (European and Mediterranean Plant Protection Organization), guideline PP 1/95(3). The experimental plots which had slugproof boundaries had a size of 1.15×1.15 m and were at least 2 m away from one another. For each element of the experiment, four repetitions were set up. 13 feed plants (lettuce, BBCH 13-14) were planted in each of the plots. Completely eaten plants were replaced by cucumber slices. The slugs were offered daytime hideouts in the form of three small boards (10 cm×20 cm) per plot. One day later, the slug pellet formulations were broadcast at 5 g/m$^2$ over the experimental area and 13 slugs of the *Arion lusitanicus* species were placed in. As an approved comparative composition, Ferramol slug pellets (approval number 024496-00, 5 g/m$^2$) was used.

Table 3 below shows the slug mortality (in percent) and the feeding damage (in percent) after x days (DAT). The phytotoxicity is reflected by the damage to the plants which has been caused by the compositions.

TABLE 3

| Formulation | Mortality % | Feeding damage % | DAT | Phytotox. |
|---|---|---|---|---|
| 2A | 15.4 | 2.1 | 2 | zero |
| 2A | 61.5 | 5.5 | 4 | zero |
| 2A | 80.8 | 5.9 | 7 | zero |
| 2A | 100.0 | 4.4 | 14 | zero |

TABLE 3-continued

| Formulation | Mortality % | Feeding damage % | DAT | Phytotox. |
|---|---|---|---|---|
| none[1] | 0.0 | 37.8 | 2 | — |
| none | 5.8 | 72.6 | 4 | — |
| none | 19.2 | 78.5 | 7 | — |
| none | 26.9 | 80.0 | 14 | — |
| Ferramol ®[2] | 25.0 | 0.0 | 2 | zero |
| Ferramol ®[2] | 88.5 | 0.3 | 4 | zero |
| Ferramol ®[2] | 100 | 0.1 | 7 | zero |
| Ferramol ®[2] | 100 | 0.1 | 14 | zero |

[1] "none" = untreated plots for comparison
[2] Ferramol ® slug pellets, trademark of W. Neudorff GmbH KG, Emmerthal/Germany

The invention claimed is:

1. A bait formulation in solid form comprising:
   a) 0.01 to 5% by weight, based on the total weight of the bait formulation, of at least one iron salt, wherein the iron salt is iron(III) phosphate;
   b) 0.01 to 5% by weight, based on the total weight of the bait formulation, of a compound selected from the group consisting of methylglycine-N,N-diacetic acid, an alkali metal salt thereof, an alkaline earth metal salt thereof, an ammonium salt thereof, and mixtures thereof;
   c) 60 to 99.89% by weight, based on the total weight of the bait formulation, of at least one starch-containing compound; and
   d) 0.01 to 0.19% by weight, calculated as the free acid and based on the total weight of the bait formulation, of a compound selected from the group consisting of ethylene-1,2-diamino-N,N,N,N-tetraacetic acid, a salt thereof and a mixture thereof.

2. The bait formulation according to claim 1, wherein the by weight of the iron salt recited in a) is calculated as Fe.

3. The bait formulation according to claim 1, wherein the % by weight of the compound recited in b) is calculated as free acid.

4. The bait formulation according to claim 1, further comprising: e) a compound selected from the group consisting of glutamine-N,N-diacetic acid, an alkali metal salt thereof, an alkaline earth metal salt thereof, an ammonium salt thereof, and mixtures thereof.

5. The bait formulation according to claim 4, wherein the weight ratio of the compound recited in b) to the compound recited in e), based in each case on the free acids, is in the range from 1:0.3 to 1:20.

6. The bait formulation according to claim 4, wherein the compound recited in e) is present in the bait formulation at a concentration of 0.01 to 2.5% by weight, calculated as the free acid and based on the total weight of the bait formulation, and wherein the total concentration of the compound recited in b) and the compound recited in e) in the bait formulation is in the range from 0.11 to 5% by weight, calculated in each case as the free acid and based on the total weight of the bait formulation.

7. A bait formulation in solid form comprising:
   a) 0.1 to 0.9% by weight, based on the total weight of the bait formulation, of iron in the form of the at least one iron salt, wherein the iron salt is iron (III) phosphate;
   b) 0.2 to 1.8% by weight, based on the total weight of the bait formulation, of a compound selected from the group consisting of methylglycine-N,N-diacetic acid, an alkali metal salt thereof, an alkaline earth metal salt thereof, an ammonium salt thereof, and mixtures thereof;
   c) 75 to 99.7% by weight, based on the total weight of the bait formulation, of at least one starch-containing component; and
   d) 0.01 to 0.19% by weight, calculated as the free acid and based on the total with of the bait formulation, of a compound selected from the group consisting of ethylene-1,2-diamino-N,N,N,N-tetraacetic acid, a salt thereof and a mixture thereof.

8. The bait formulation according to claim 1, additionally comprising at least one protein-containing substance.

9. The bait formulation according to claim 1, additionally comprising glucose and/or a glucose-containing disaccharide.

10. The bait formulation according to claim 1, in the form of particles having mean dimensions in the range from 0.5 to 6 mm.

11. A method for control of terrestrial slugs and snails comprising contacting a terrestrial slug or snail with a bait formulation according to claim 1.

12. The method for controlling terrestrial slugs- and snails according to claim 11, wherein the bait formulation is deployed in the habitat of the slug or snail.

13. The bait formulation according to claim 1, further comprising: e) 0.1 to 15% by weight, based on the total weight of the bait formulation, of a compound selected from the group consisting of glutamine-N,N-diacetic acid, an alkali metal salt thereof, an alkaline earth metal salt thereof, an ammonium salt thereof, and mixtures thereof, wherein the total concentration of the compound recited in b) and the compound recited in e), calculated in each case as the free acid and based on the total weight of the bait formulation, is in the range from 0.11 to 5% by weight.

14. The bait formulation according to claim 7, further comprising: e) 0.1 to 1%-by weight, based on the total weight of the bait formulation, of a compound selected from the group consisting of glutamine-N,N-diacetic acid, an alkali metal salt thereof, an alkaline earth metal salt thereof, an ammonium salt thereof, and mixtures thereof, wherein the total concentration of the compound recited in b) and the compound recited in e), calculated in each case as the free acid and based on the total weight of the bait formulation, is in the range from 0.2 to 1.8% by weight.

* * * * *